United States Patent [19]

Scherz et al.

[11] Patent Number: 5,510,361
[45] Date of Patent: Apr. 23, 1996

[54] DI-TERT-BUTYLPHENOL COMPOUNDS WITH HETEROCYCLIC MOIETY, USEFUL AS ANTI-INFLAMMATORY AGENTS

[75] Inventors: Michael W. Scherz, West Chester; Stanislaw Pikul, Cincinnati, both of Ohio

[73] Assignee: The Procter & Gamble Company, Cincinnati, Ohio

[21] Appl. No.: 326,619

[22] Filed: Oct. 20, 1994

[51] Int. Cl.[6] .......................... A61K 31/41; A61K 31/42; C07D 231/06; C07D 261/04
[52] U.S. Cl. .......................... 514/378; 514/403; 548/240; 548/379.1
[58] Field of Search ................................ 548/240, 379.1; 514/378, 403

[56] References Cited

U.S. PATENT DOCUMENTS

| | | | |
|---|---|---|---|
| 4,239,901 | 12/1980 | Rainer | 560/34 |
| 4,535,165 | 8/1985 | Moore | 548/204 |
| 4,724,246 | 2/1988 | Ravichandran | 524/83 |
| 4,808,620 | 2/1989 | Oe et al. | 514/303 |
| 4,891,374 | 1/1990 | Thorwart et al. | 514/222 |
| 4,908,364 | 3/1990 | Thorwart et al. | 514/243 |
| 4,940,790 | 7/1990 | Thorwart et al. | 544/8 |
| 4,996,327 | 2/1991 | Merkle et al. | 548/378 |
| 5,155,122 | 10/1992 | Connor et al. | 514/363 |
| 5,208,251 | 5/1993 | Belliotti et al. | 514/372 |

FOREIGN PATENT DOCUMENTS

| | | |
|---|---|---|
| 58-148858 | 9/1983 | Japan . |
| 1-180878 | 7/1989 | Japan . |
| 2-229169 | 9/1990 | Japan . |

OTHER PUBLICATIONS

Costantino, L., C. Parenti, M. DiBella, P. Zanoli and M. Baraldi, "Anti-inflammatory Activity of Newly Synthesized 2,6—Bis—(1,1—dimethylethyl)phenol Derivatives", *Pharmacological Research*, vol. 27 (1993), No. 4, pp. 349–357.

Isomura, Y., S. Sakamoto, N. Ito, H. Homma, T. Abe and K. Kubo, "Synthesis and Anti–inflammatory Activity of 2,6—Di—tert—butylphenois with a Heterocyclic Group at the 4–Position. III.", *Chem. Pharm. Bull.*, vol. 32 (1984), No. 1, pp. 152–165.

Mullican, M. D., M. W. Wilson, D. T. Connor, C. R. Kostlan, D. J. Schrier and R. D. Dyer "Design of 5—(3,5—Di—tert—butyl—4—hydroxyphenyl)—1,3,4—thiadiazoles, —1,3,4—oxadiazoles, and —d1,2,4—triazoles as Orally–active, Nonulcerogenic Antiinflammatory Agent", *J. Med. Chem.*, vol. 36 (1993), No. 8, pp. 1090–1099.

Unangst, P. C., G. P. Shrum, D. T. Connor, R. D. Dyer and D. J. Schrier "Novel 1,2,4—Oxadiazoles and 1,2,4—Thiadiazoles as Dual 5—Lipoxygenase and Cycloxygenase Inhibitors", *J. Med. Chem.*, vol. 35 (1992), No. 20, pp. 3691–3698.

*Primary Examiner*—Joseph K. McKane
*Attorney, Agent, or Firm*—Milton B. Graff, IV; Karen F. Clark; Mary Pat McMahon

[57] ABSTRACT

The subject invention relates to compounds having the structure:

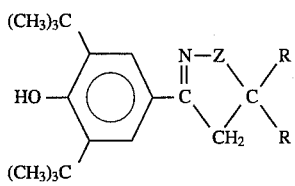

wherein a) each R is independently alkyl having from 1 to about 7 carbon atoms;

b) Z is O or N—X;

c) X is selected from hydrogen, alkyl having from 1 to about 7 carbon atoms, C(O)Y, C(S)Y, and $SO_2Y$;

d) Y is selected from R', OR' and $NR'_2$; and e) R' is selected from hydrogen, alkyl having from 1 to about 7 carbon atoms, and phenyl.

The subject invention also relates to pharmaceutical compositions comprising the above compounds, and methods of treating inflammation or pain using the compounds.

14 Claims, No Drawings

DI-TERT-BUTYLPHENOL COMPOUNDS WITH HETEROCYCLIC MOIETY, USEFUL AS ANTI-INFLAMMATORY AGENTS

TECHNICAL FIELD

The subject invention relates to nonsteroidal anti-inflammatory drugs, particularly to substituted di-tert-butylphenol compounds.

BACKGROUND OF THE INVENTION

Certain di-tert-butylphenol compounds and other compounds structurally related thereto have been found to have significant anti-inflammatory and/or analgesic activity; others have been found to have other disease altering activities. Certain of such compounds, processes for making them, and uses for them are disclosed in the following references: U.S. Pat. Nos. 4,535,165 issued to Moore on Aug. 13, 1985; 4,724,246 issued to Ravichandran on Feb. 9, 1988; 4,808,620 issued to Oe, Kawasaki, Terasawa & Yasunaga on Feb. 28, 1989; 4,891,374 issued to Thorwart, Gebert, Schleyerbach & Bartlett on Jan. 2, 1990; 4,908,364 issued to Thorwart, Gebert, Schleyerbach & Bartlett on Mar. 13, 1990; 4,940,790 issued to Thorwart, Gebert, Schleyerbach & Bartlett on Jul. 10, 1990; 5,155,122 issued to Connor, Flynn, Kostlan, Mullican, Shrum, Unangst & Wilson on Oct. 13, 1992; Japanese Patent Application Nos. 58-148858 of Yamanouchi Pharm. Co. published on Sep. 5, 1983; 1-180878 of Yoshitomi Pharm. Ind. published Jul. 18, 1989; 2-229169 of Takeda Chemical Ind. published Sep. 11, 1990: Isomura, Y., S. Sakamoto, N. Ito, H. Homma, T. Abe & K. Kubo, "Synthesis and Anti-inflammatory Activity of 2,6-Di-tert-butylphenols with a Heterocyclic Group at the 4-Position. III.", *Chem. Pharm. Bull.*, Vol. 32 (1984) No. 1, pp. 152–165; Unangst, P. C., G. P. Shrum, D. T. Connor, R. D. Dyer & D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; Costantino, L., C. Parenti, M. Di Bella, P. Zanoli & M. Baraldi, "Anti-inflammatory Activity of Newly Synthesized 2,6-Bis-(1,1-Dimethylethyl)Phenol Derivatives", *Pharmacological Research*, Vol. 27 (1993) No. 4, pp. 349–358; Mullican, M. D., M. W. Wilson, D. T. Connor, C. R. Kostlan, D. J. Schrier & R. D. Dyer, "Design of 5-(3,5-Di-tert-butyl-4-hydroxyphenyl)-1,3,4-thiadiazoles,-1,3,4-oxadiazoles, and- 1,2,4-triazoles as Orally-Active, Nonulcerogenic Anti-inflammatory Agents", *J. Med. Chem.*, Vol. 36 (1993), pp. 1090–1099.

Although a number of di-tert-butylphenol compounds have been demonstrated to exhibit anti-inflammatory activity, many such compounds exhibit little or no anti-inflammatory activity. Thus it is generally not possible to predict whether such compounds have substantial anti-inflammatory activity without testing for the activity.

It is an object of the subject invention to provide compounds which have effective anti-inflammatory, analgesic and/or anti-oxidant activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention involves compounds having the structure:

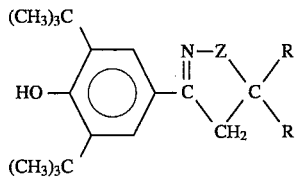

wherein
a) each R is independently alkyl having from 1 to about 7 carbon atoms;
b) Z is O or N—X;
c) X is selected from hydrogen, alkyl having from 1 to about 7 carbon atoms; C(O)Y, C(S)Y, and $SO_2Y$;
d) Y is selected from R', OR' and $NR'_2$; and
e) each R' is selected from hydrogen, alkyl having from 1 to about 7 carbon atoms, and phenyl.

DETAILED DESCRIPTION OF THE INVENTION

As used herein, unless otherwise indicated, "alkyl" means a straight, branched or cyclic hydrocarbon chain, saturated or unsaturated, unsubstituted or substituted. Preferred alkyl are straight chain. Preferred branched alkyl have one or two branches, preferably one branch. Preferred cyclic alkyl are monocyclic or are straight chain and monocyclic combination, especially a straight chain with a monocyclic terminus. Preferred alkyl are saturated. Unsaturated alkyl have one or more double bonds or/and one or more triple bonds. Preferred unsaturated alkyl have one or two double bonds or one triple bond, more preferably one double bond. Preferred alkyl are unsubstituted. Preferred substituted alkyl are mono-, di-, or trisubstituted, more preferably monosubstituted. Preferred alkyl substituents include halo, hydroxy, alkoxy (e.g., methoxy, ethoxy propoxy, butoxy, pentoxy), aryloxy (e.g., phenoxy, chlorophenoxy, tolyloxy, methoxyphenoxy, alkyloxycarbonylphenoxy, acyloxyphenoxy), benzyloxy, acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, alkyloxycarbonylphenylthio), benzylthio, aryl (e.g., phenyl, tolyl, alkyloxyphenyl, alkyloxycarbonylphenyl, carboxyphenyl, halophenyl), heterocyclyl, heteroaryl, amino (e.g., amino, mono-and di- $C_1$–$C_3$ alkanylamino, methylphenylamino, methylbenzylamino), amido (e.g., amido, mono- and di- $C_1$–$C_3$ alkanylamido, carbamamido), ureido and guanidino.

As used herein, "alkanyl" means a saturated alkyl.

As used herein, "alkoxy" means a substituent having the structure Q—O—, where Q is alkyl.

As used herein, "alkylthio" means a substituent having the structure Q—S—, where Q is alkyl.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include hydroxy, mercapto, halo, methyl, ethyl and propyl.

As used herein, "heterocyclyl" means a moiety having a saturated or unsaturated non-aromatic ring having from 3 to about 8 ring atoms, including from 2 to about 6 carbon atoms and from 1 to about 4 heteroatoms selected from O, S, and N. Preferred heterocycles are saturated. Preferred heterocycles have 5 or 6 atoms in the ring including 1 to 3 heteroatoms in the ring, also preferably 1 or 2 heteroatoms in the ring. Specific preferred heterocycles include piperidinyl, tetrahydrothienyl, pyrrolidinyl, piperazinyl, morpholinyl, tetrahydropyranyl, tetrahydrofuranyl, imidazolidinyl, pyrazolidinyl, oxazolidinyl, isoxazolidinyl, oxathiazolidinyl, isothiazolidinyl, azepinyl, oxepinyl, triazolidinyl. Heterocycles are unsubstituted or substituted, preferably unsubstituted. Preferred substituted heterocycles are mono-, di-, or trisubstitued, more preferably monosubstituted. Preferred heterocycle substitutents include alkyl (including substituted alkyl, e.g., thiomethyl, carboxymethyl, chloromethyl, trifluoromethyl), halo, hydroxy, carboxy, alkoxy, acyloxy, mercapto, amino (including mono- and di- $C_1$–$C_3$ alkanylamino, e.g., methylamino, dimethylamino), amido, carbamamido, thiocarbamamido, ureido, thioureido, guanidino (including methyl-substituted guanidino, e.g., methylguanidino, N,N'-dimethylguanidino, N,N-dimethylguanidino).

As used herein, "heteroaryl" means a moiety having an aromatic ring having 5 or 6 ring atoms including from 2 to 5 carbon atoms and from 1 to 4 heteroatoms selected from O, S and N. More preferred heteroaryls have 1 to 3 heteroatoms in the ring, also preferably 1 or 2 heteroatoms in the ring. Specific preferred heteroaryls include pyrrolyl, imidazolyl, pyridyl, pyrimidinyl, pyrazinyl, oxazolyl, isoxazolyl, pyranyl, thienyl, tetrazolyl, thiazolyl, isothiazolyl, furyl, oxathiazolyl. Heteroaryls are unsubstituted or substituted, preferably unsubstituted. Preferred substituted heterocycles are mono-, di-, or trisubstituted, more preferably monosubstituted. Preferred heteroaryl substituents include alkyl, (including substituted alkyl, e.g., thiomethyl, carboxymethyl, chloromethyl, trifluoromethyl), halo, hydroxy, alkoxy, thio, amino (including mono- and di- $C_1$–$C_3$ alkanylamino, e.g., methylamino, dimethylamino, methoxymethylamino, carboxymethylamino), amido, cyanamido, thiocarbamamido, ureido, thioureido, guanidino (including methyl-substituted guanidino, e.g., methylguanidino, N,N'-dimethylguanidino, N,N'-dimethylguanidino), N,N-dimethylguanidino), S-methylthiocarbamoyl.

As used herein, "halo" means fluoro, chloro, bromo or iodo; preferred halo are fluoro, chloro and bromo; more preferred is chloro, and also fluoro.

Compounds

The subject invention involves particular di-tert-butylphenol compounds having the following structure:

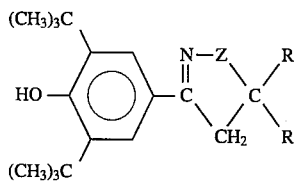

In the above structure, each R is independently alkyl having from 1 to about 7 carbon atoms, preferably from 1 to about 4 carbon atoms. Each R is preferably saturated. Each R is preferably unsubstitutted. Each R is preferably $C_1$ to about $C_3$ straight or branched alkanyl, or $C_3$ to about $C_4$ cyclic alkanyl. Each R is preferably methyl, ethyl, n-propyl or i-propyl; more preferably methyl or ethyl; most preferably methyl. Each R is also preferably cyclopropyl. Preferably, both R are the same moiety.

In the above structure, Z is O or N—X; preferred Z is oxygen. X is selected from hydrogen, alkyl having from 1 to about 7 carbon atoms, C(O)Y, C(S)Y, and $SO_2Y$. Preferred X is hydrogen. Also preferred X is $SO_2Y$.

Y is selected from R', OR' and NR'$_2$. Preferred Y is R'. Also preferred Y is NR'$_2$. R' is selected from hydrogen, alkyl having from 1 to about 7 carbon atoms, and phenyl. Preferred R' is hydrogen or $C_1$–$C_4$ alkyl. More preferred R' is selected from hydrogen, methyl, ethyl, n-propyl, i-propyl, and cyclopropyl; most preferred is hydrogen or methyl.

Preferred compounds of the subject invention include those having the above structure with R, Z, X, Y and R' as indicated in the following table:

| Compound No. | R | Z | X | Y | R' |
|---|---|---|---|---|---|
| 1 | Me, Me | O | — | — | — |
| 2 | Me, Me | N-X | H | — | — |
| 3 | Me, Me | N-X | $SO_2Y$ | R' | Me |
| 4 | Me, Me | N-X | C(O)Y | NR'$_2$ | H, H |
| 5 | c-Pr, c-Pr | N-X | H | — | — |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, antiarthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G.G.I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Codex in the Pathogenesis of Arthritis", *British Medical Journal*, Vol. 2 (1949), pp. 1129–1135; and Winter, C.A., E.A. Risley & G.W. Nuss, "Carrageenan-lnduced Edema in Hind Paw of the Rats as an Assay for Anti-inflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Anti-inflammatory Drugs",

*Nonsteroidal Anti-inflammatory Drugs*, Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch. Int. Pharmacodyn.*, Vol. 169, No. 2 (1967) pp. 384–393; Milne, G. M. & T. M. Twomey, "The Analgetic Properties of Piroxicam in Animals and Correlation with Experimentally Determined Plasma Levels", *Agents and Actions*, Vol. 10, No. 1/2 (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs, even compared to many other di-tert-butylphenol derivatives. Some compounds of the subject invention are even gastroprotective, protecting the stomach from ulcers and erosions, particularly those caused by ethanol or other NSAIDs.

Certain NSAIDs, including certain di-tert-butylphenol derivatives, when dosed systemically, cause an undesirable increase in systemic levels of certain liver enzymes. Compounds of the subject invention generally cause little or no liver enzyme side effects.

Compounds useful in the subject invention can be made using the following general reaction schemes:

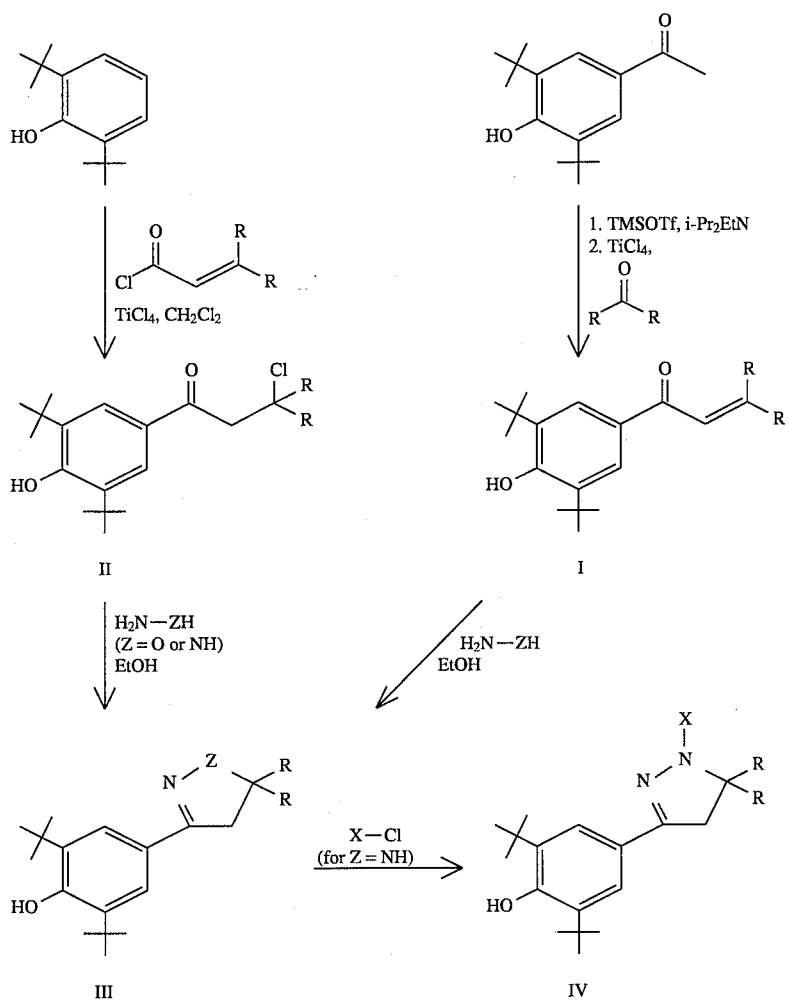

A general method for the preparation of compounds with general structure III, when Z is O is the cyclo-condensation reaction with hydroxyl amine of an appropriate β-chloroketone of general structure II. For example, this reaction can be performed by slow treatment of an alcoholic solution of the appropriate β-chloroketone and hydroxylamine hydrohalide salt with a stoichiometric amount of aqueous NaOH. Compounds of general structure III, when Z is NH, can be prepared by cyclocondensation of α,β-unsaturated ketones of general structure I with hydrazine. For example, this reaction can be performed by heating an alcoholic solution of an appropriate α,β-unsaturated ketone and a stoichiometric quantity of hydrazine hydrate at temperatures between 30° C. and 60° C. If higher reaction temperatures are desired, the reaction can be performed in a sealed flask. The necessary β-chloroketones and α,β-unsaturated ketones are conveniently prepared by Friedel-Crafts reaction of 2,6-di-tert-butylphenol with an appropriate α,β-unsaturated acid chloride followed by exposure to excess hydrochloric acid, or by aldol condensation of silylated 3,5-di-tert-butyl-4-hydroxyacetophenone with an appropriate ketone under the influence of $TiCl_4$.

The following non-limiting examples provide further information regarding synthesis of the subject compounds.

EXAMPLE 1

Synthesis of 3-(3,5-di-tert-butyl-4-hydroxyphenyl)-4,5-dihydro-5,5-dimethyl-isoxazole:

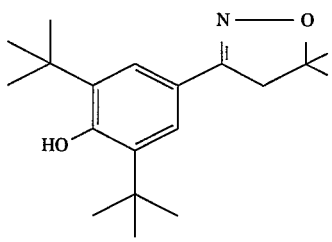

3-Chloro-1-(3,5-di-tert-butyl-4-hydroxyphenyl)-3-methylbutan-1-one. In a 12 L round bottom flask, equipped with internal thermometer, mechanical stirrer, addition funnel and septum inlet, is placed a solution of 3,3-dimethylacryloyl chloride (146 g, 1.23 mol) in $CH_2Cl_2$ (1000 mL). The stirred solution is cooled in a $CH_2Cl_2$-dry ice bath to −10° C., and then $TiCl_4$ (1M in $CH_2Cl_2$, 1476 mL, 1.47 mol, 1.2 eq) is added via canula at a rate such that the reaction mixture does not warm above −5° C. The solution is stirred for 10 min after addition is complete, and then a solution of 2,6-di-tert-butylphenol (253.4 g, 1.23 mol, 1.0 eq) in $CH_2Cl_2$ (500 mL) is added dropwise via addition funnel. The rate of addition is adjusted to maintain the reaction temperature below 0° C. After addition is complete, the cold bath is removed, and the mixture is allowed to stir at ambient temperature for 4 h. TLC analysis (EtOAc:hexane, 1:9) indicates the reaction to be complete. $H_2O$ (2 L) is added carefully, and the mixture is transferred to a 6 L extraction funnel. The organic phase is separated, washed with additional $H_2O$ (2×1000 mL), dried over $Na_2SO_4$, filtered, and returned to the 12 L reaction vessel. Ethereal HCl (1M, Aldrich, 2000 mL) is added. After stirring 2 h, the solution is transferred to the 6 L separatory funnel, and washed with $H_2O$ (3×1 L). The organic phase is dried over $Na_2SO_4$, filtered into a 10-L round bottom flask, and rotary evaporated. The residue is taken up in 1 L pentane, and kept at −4° C. overnight. The resulting crystalline solid is filtered off and dried to give 3-chloro-1-(3, 5-di-tert-butyl-4-hydroxyphenyl )-3-methylbutan-1-one.

3-(3,5-Di-tert-butyl-4-hydroxyphenyl)-4,5-dihydro-5,5-dimethylisoxazole. In a 5 L round bottom flask, equipped with magnetic stirrer and Ar inlet is placed a solution of (77.1 g, 0.24 mol) 3-chloro-1-(3,5-di-tert-butyl-4-hydroxyphenyl)-3-methylbutan- 1one and hydroxylamine hydrochloride (20.1 g, 0.28 mol) in EtOH (2.2 L). To the stirred solution is added 2 N NaOH (119 mL,0.24 mol, 1.0 eq) dropwise over 15 min. A rapidly dissipating yellow color is observed on contact of the two solutions. After addition is complete, the reaction is heated at 50° C. The reaction is followed by TLC (EtOAc:hexane, 1:4). After 3 hr, approximately 50% conversion is achieved. The crude product is precipitated by addition of $H_2O$ (750 mL), and filtered. The filtrate is set aside. A single recrystallization of the solids from hexane provides 3-(3,5-di-tert-butyl-4-hydroxyphenyl)-4,5-dihydro-5,5-dimethylisoxazole as a faint yellow solid. The $H_2O$/EtOH filtrate is concentrated on a rotary evaporator to remove EtOH, and the resulting suspension is extracted with $CH_2Cl_2$ (3×200 mL). The aqueous phase is discarded, and the organic phase is dried ($MgSO_4$), filtered, combined with the hexane mother liquor from the above crystallization, and evaporated to an oily solid. Crystallization from hexane produces 3-(3,5-di-tert-butyl-4-hydroxyphenyl)4,5dihydro-5,5-dimethylisoxazole as a yellow solid slightly less pure than the first batch.

EXAMPLE 2

Synthesis of 3-(3,5-di-tert-butyl-4-hydroxyphenyl)-5,5-dimethyl-1H-di-hydropyrazole:

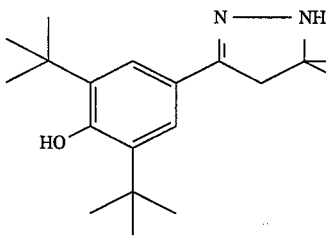

A solution of 3-chloro-1-( 3,5-di-tert-butyl-4-hydroxyphenyl)-3-methylbutan-1one (Example 1) (3.45 g, 10.1 mmol) and hydrazine hydrate (0.8 mL, 14 mmol) in absolute EtOH (50 mL) is stirred at 50° C. for 1 hr. Additional hydrazine hydrate (1 mL, 18 mmol) is added in two equal portions over 2 hr. The reaction is followed by TLC (hexane:EtOAC, 9:1) and is complete after stirring at 50° C. for 18 hr. The solvent is evaporated leaving a yellow solid, which is crystallized from EtOH:$H_2O$ to yield 3-(3, 5-di-tert-butyl-4-hydroxyphenyl )-5,5-dimethyl- 1 H-dihydropyrazole as white prisms.

EXAMPLE 3

Synthesis of 3-(3,5-di-tert-butyl-4-hydroxyphenyl)-5,5-dimethyl-1-methylsulfonyl-1H-dihydropyrazole:

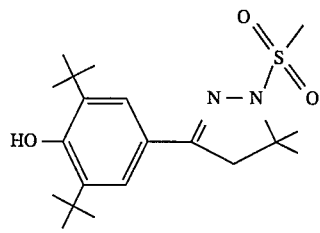

To a stirred solution of 650 mg of 3-(3,5-di-tert-butyl-4-hydroxyphenyl)-5,5-dimethyl-1H-dihydropyrazole (Example 2), 360 µl of triethylamine, 50 mg of N,N-dimethylaminopyridine in 20 ml of methylene chloride, cooled to 0° C., is added 182 µl of methanesulphonyl chloride. After stirring at 0° C. for 30 min the cooling bath is removed and the mixture is stirred at room temperature for 2 hrs. The solvent is evaporated under reduced pressure and the residue is purified by flash chromatography (10% ethyl acetate in hexane) to give 3-(3,5-di-tert-butyl-4-hydroxyphenyl)-5,5-dimethyl- 1-methylsulfonyl-1H-dihydropyrazole as a colorless solid.

EXAMPLE 4

Synthesis of 1-carboxamido-3-(3,5-di-tert-butyl-4-hydroxyphenyl)-5,5-dimethyl-1H-dihydropyrazole:

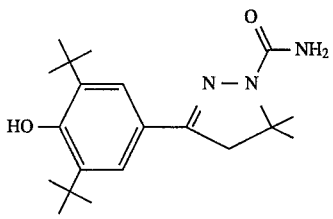

To a stirred solution of 600 mg of 3-(3,5-di-tert-butyl-4-hydroxyphenyl)-5,5-dimethyl-1H-dihydropyrazole (Example 2), in a mixture of 9 ml of acetic acid, 6.5 ml of tetrahydrofuran and 18.6 ml of water at 35° C., is added 260 mg of potassium cyanate. After stirring at 35° C. for 30 min the mixture is stirred at 55° C. for 5 hrs. The solvents are evaporated under reduced pressure and the residue is taken up in 50 ml of methylene chloride. The solution is washed 3 times with 15 ml of 0.1N aqueous sodium hydroxide and dried over sodium sulphate. The solvents are evaporated and the residue is purified by flash chromatography (20% ethyl acetate in hexane) to give 1-carboxamido-3-(3,5-di-tert-butyl-4-hydroxyphenyl)5,5-dimethyl- 1H-dihydropyrazole as a colorless solid.

EXAMPLE 5

Synthesis of 3-(3,5-di-tert-butyl-4-hydroxyphenyl)-5,5-dicyclopropyl-1H-dihydropyrazole:

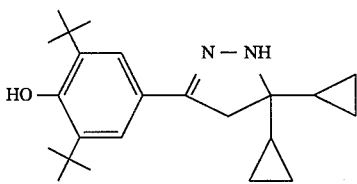

1-(3,5-di-tert-butyl-4-hydroxyphenyl)-3,3-dicyclopropyl-prop2-en-1-one. A stirred solution of 4 g of 3,5-di-tert-butyl-4-hydroxyacetophenone in 250 ml of dry methylene chloride is cooled to −78° C. and 7.3 ml di-iso-propyl ethylamine (i-Pr$_2$EtN) is added followed by 8.1 ml of trimethylsilyl trifluoromethanesulphonate (TMSOTf). The mixture is stirred at −78° C. for 10 minutes and is allowed to warm to ambient temperature over 1 hour. The mixture is cooled again to −78° C., and 3.6 ml of dicyclopropylketone is added followed by 32 ml of 1M titanum tetrachloride solution in methylene chloride. After stirring for 1 hr, the mixture is washed with 1N aqueous hydrochloric acid and the solvents are removed under reduced pressure. The residue is dissolved in 50 ml of methanol-1N aqueous hydrochloric acid and stirred for 1 hr at room temperature. The mixture is concentrated under reduced pressure and partitioned between methylene chloride and water. The organic phase is washed with aqueous sodium bicarbonate, brine and dried over sodium sulphate. The solvents are evaporated and the residue is purified by flash chromatography (10% ethyl acetate in hexane), and the product is recrystallized from hexane to give 1-(3,5-di-tert-butyl-4-hydroxyphenyl)- 3,3-dicyclopropylprop-2-en-1-one as an orange solid.

3-(3,5-di-tert-butyl-4-hydroxvphenyl )-5,5-dicyclopropyl- 1H-dihydropyrazole A pressure resistant glass container is charged with 350 mg of 1-(3,5-di-tert-butyl-4-hydroxyphenyl)-3,3-dicyclopropylprop-2-en-1-one, 0.2 ml of hydrazine hydrate and 15 ml of ethanol. The container is closed and the homogenous mixture is heated to 80° C. for 15 hrs. The solvents are evaporated under reduced pressure and the residue is taken up in methylene chloride, washed with water and dried over sodium sulphate. The solvents are evaporated and the crude product is purified by crystallization from hexane to give 3-(3,5-di-tert-butyl-4-hydroxyphenyl)- 5,5-dicyclopropyl-1H-dihydropyrazole as a yellow solid.

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 1000 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg.

Many of the subject compounds are hydrophobic. If it is desired to provide an aqueous-based composition or a composition soluble in or miscible with aqueous media, a solubilizing agent may be included in the composition. Nonlimiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. Nos. 5,189,066 of Kelm & Bruns, issued Feb. 23, 1993, entitled "Pharmaceutical Compositions of Tebufelone", and 5,281,420 of Kelm & Dobrozsi, issued Jan. 25, 1994, entitled "Solid Dispersion Compositions of Tebufelone", hereby incorporated herein by reference.

Methods

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for protecting against free radical damage resulting from oxidative stress and ischemic conditions by administering a safe and effective amount of a subject compound to a human or lower animal in need of such treatment. Such treatment may include protecting against ischemic heart disease, atherosclerosis, stroke, and ischemic cell damage of head.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or nonsteroidal antiinflammatory drugs (NSAIDs) can be treated and/or prevented by administration of preferred subject compounds.

Appropriate tests for determining the gastrointestinal safety or gastroprotective properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y, O. Ohya, T. Abe, T. Omata, et al., "Anti-inflammatory, Analgesic, and Antipyretic Effects and Gastrointestinal Toxicity of the New Anti-inflammatory Drug N-{3-[3-(piperidinylmethyl)phenoxy]propyl}carbamoylmethylthio]ethyl 1-(p-chlorobenzoyl) 5-Methoxy-2methyl-3indolylacetate", *Arzneim.-Forsch./Drug Res.*, Vol. 42 (1992), pp. 954–992. In the methods disclosed therein, stomachs of the animals are typically examined two hours after dosing a compound.

Methods for determining subchronic gastrointestinal safety are disclosed and/or referred to in the following references: Melarange, R., C. Gentry, et al., "Anti-inflammatory and Gastrointestinal Effects of Nabumetone or Its Active Metabolite, 6-Methoxy-2-naphthylacetic Acid (6 MNA)", *Dig. Dis. Sci.*, Vol. 37 (1992), pp. 1847–1852; and Wong, S., S. J. Lee, et al., "Antiarthritic Profile of BF-389—A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharirinduced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm² to about 200 mg/cm² of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

The following non-limiting examples illustrate the subject invention.

Example A

Pharmaceutical compositions in the form of tablets are prepared by conventional methods, such as mixing and direct compaction, formulated as follows:

| Ingredient | Quantity (mg per tablet) |
|---|---|
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Example B

A pharmaceutical composition in capsule form is prepared by conventional methods, formulated as follows:

| Ingredient | Quantity (mg per capsule) |
|---|---|
| Compound 5 | 200 |
| Lactose | To fill to volume of capsule |

The above capsule administered orally once a day substantially reduces the symptomology of a patient afflicted with rheumatoid arthritis or osteoarthritis.

Example C

A pharmaceutical composition in liquid form is prepared by conventional methods, formulated as follows:

| Ingredient | Quantity |
|---|---|
| Compound 2 | 200 mg |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

Example D

A pharmaceutical composition in liquid form is prepared by conventional methods, formulated as follows:

| Ingredient | Quantity |
|---|---|
| Microcrystalline (micronized) Compound 3 | 200 mg |
| Avicel (microcrystalline cellulose) | 50 mg |
| Tween 80 | 1.6 ml |
| Methyl cellulose | 0.4 mg |
| Deionized water | 80 ml |

100 ml of the above composition administered perorally twice a day substantially reduces the symptoms of a patient afflicted with rheumatoid arthritis or osteoarthritis.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

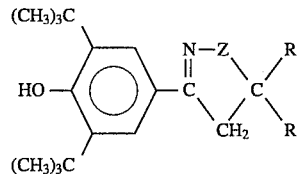

wherein a) each R is independently substituted or unsubstituted cycloalkyl or alkyl having from 1 to about 7 carbon atoms;

b) Z is O or N—X;

c) X is selected from the group consisting of hydrogen, alkyl having from 1 to about7 carbon atoms, C(O)Y, C(S)Y, and SO2Y;

d) Y is selected from the group consisting of R', OR'and NR'$_2$; and e) R' is selected from the group consisting of hydrogen, alkyl having from 1 to about 7 carbon atoms, and phenyl.

2. The compound of claim 1 wherein Z is oxygen.

3. The compound of claim 1 wherein each R is unsubstituted $C_1$–$C_3$ alkanyl.

4. The compound of claim 3 wherein Z is oxygen.

5. The compound of claim 3 wherein both R are the same moiety.

6. The compound of claim 5 wherein both R are methyl, and Z is oxygen.

7. The compound of claim 3 wherein Z is N—X.

8. The compound of claim 7 wherein X is hydrogen or unsubstituted $C_1$–$C_3$ alkanyl, and both R are the same moiety.

9. The compound of claim 7 wherein X is selected from the group consisting of C(O)Y, C(S)Y, and SO2Y; R' is hydrogen or unsubstituted $C_1$–$C_3$ alkanyl; and both R are the same moiety.

10. The compound of claim 9 wherein X is $SO_2Y$, and Y is unsubstituted $C_1$–$C_3$ alkanyl.

11. The compound of claim 10 wherein Y is methyl and both R are methyl.

12. The compound of claim 8 wherein both R are methyl.

13. A pharmaceutical composition comprising:
(a) a safe and effective amount of the compound of claim 1, 4, 6, 8, or 9; and
(b) a pharmaceutically-acceptable carrier.

14. A method of treating inflammation or pain comprising the peroral administration of a safe and effective amount of the compound of claim 1, 4, 6, 8 or 9.

* * * * *